United States Patent [19]

Uchida et al.

[11] Patent Number: Plant 6,187

[45] Date of Patent: May 24, 1988

[54] CARNATION PLANT NAMED JUN

[75] Inventors: Jun J. Uchida, Salinas; Barbara J. Grotta, Fremont, both of Calif.

[73] Assignee: California Florida Plant Company, Fremont, Calif.

[21] Appl. No.: 838,927

[22] Filed: Mar. 12, 1986

[51] Int. Cl.[4] ..... A01H 5/00

[52] U.S. Cl. ..... Plt./71

[58] Field of Search ..... Plt./71

*Primary Examiner*—Robert E. Bagwill

*Attorney, Agent, or Firm*—James R. Cypher

[57] ABSTRACT

The present invention relates to a new and distinct cultivar of Carnation Plant named Jun Sakura, a sport of Scania, distinguished from its closest commercial variety, Soana Baranna, as well as any other variety known to me, by its darker pink flower color, taller plant habit, darker foliage color, earlier flowering response, resistance to color fading, a higher crowned flower of larger diameter and less splitting of the calyx and bullheading under widely fluctuating temperatures.

3 Drawing Sheets

BACKGROUND OF THE INVENTION

This invention relates to a new and distinct variety of carnation plant, named Jun Sakura, which is a sport of the cultivar Scania, a non-patented, commercially available, red colored carnation of the "Sim" family.

This sport was discovered and selected because of its distinct, pleasing pink color from a flowering of Scania in commercial greenhouses in Salinas, Calif. on Jan. 12, 1982. The closest commercial cultivar in color to the new sport of which I am aware is the carnation Soana Baranna, U.S. Plant Pat. No. 3,534, granted in 1974. The distinguishing characteristics which are outstanding in the new cultivar and which distinguish it from Scania and Soana Baranna are as follows:

1. It has a darker pink flower color than Soana Baranna. Scania is red.
2. It is less prone to color fading under high light, high temperature conditions than Soana Baranna.
3. Foliage is curled, darker green than Soana Baranna and is longer and broader when uncurled and measured. The foliage is typically curled as in most Sim cultivars.
4. Pinched plants are 3" to 5" taller from the same plant date than Soana Baranna.
5. Flower diameter averages 0.75 cm larger and crown is higher than Soana Baranna.
6. Bloom date is 7-10 days faster from the same plant date than Soana Baranna.
7. Flowers of Jun Sakura split and bullhead less under fluctuating temperatures than Soana Baranna.

Asexual reproduction and flowerings of this new cultivar by side shoot cuttings rooted in peat and "Perlite" under mist were performed under our direction at Fremont, Calif. in commercial greenhouses. The new cultivar was found to retain its distinctive characteristics as listed herein through successive propagations.

BRIEF DESCRIPTION OF THE DRAWING

The accompanying drawings serve, by color photographic means, to illustrate the new plant variety, Jun Sakura, in comparison to its closest known commercial variety, Soana Baranna.

DETAILED DESCRIPTION OF THE DRAWING

Figures 1, 2:
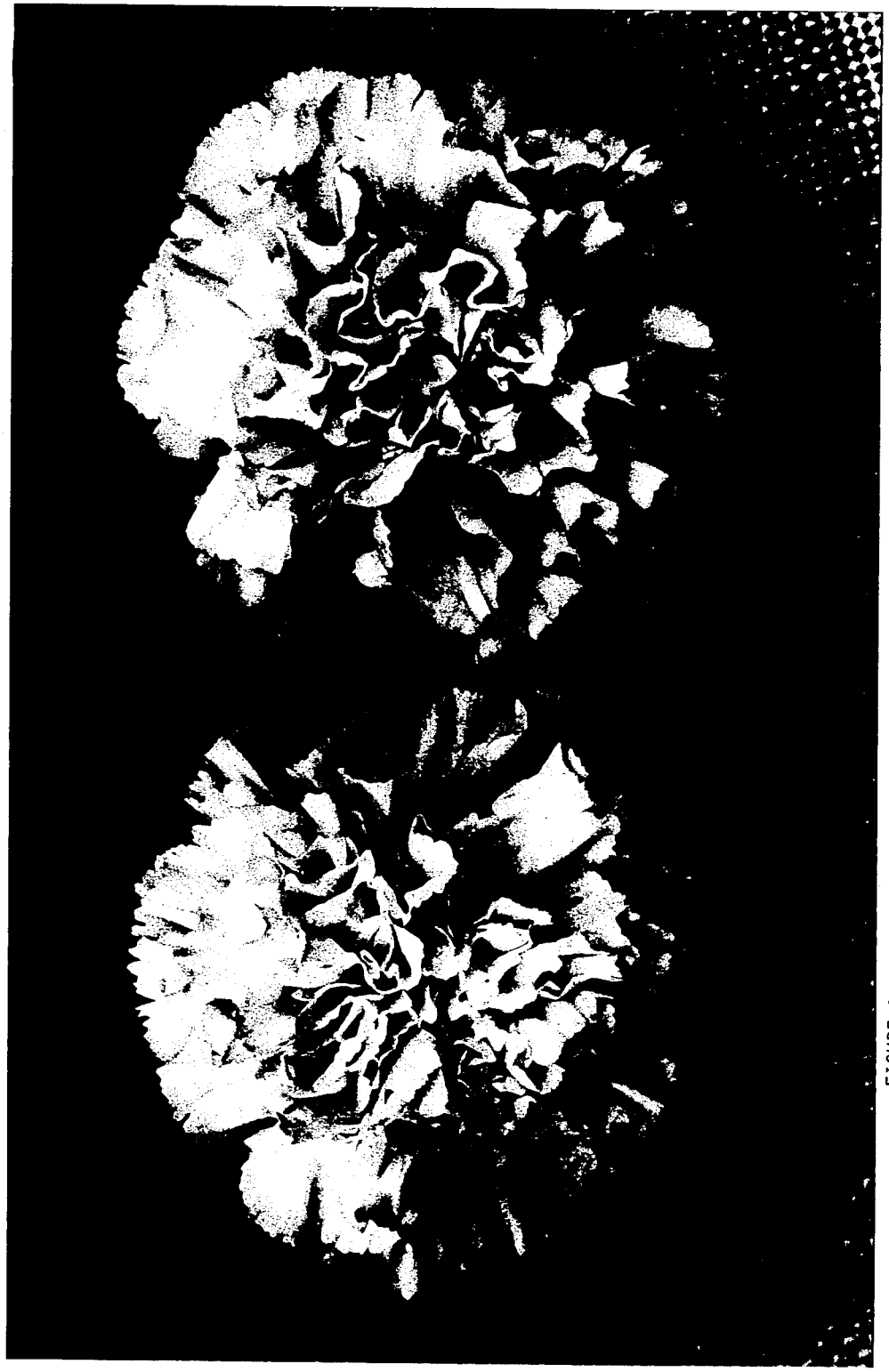
FIGURE 1 (Prior Art)
FIG. 1 is a close up view of the bloom of Soana Baranna.
FIG. 2 is a close up view of the bloom of the new cultivar, Jun Sakura. This photo shows the darker pink color of Jun Sakura and the larger bloom size.
Figures 3, 4:
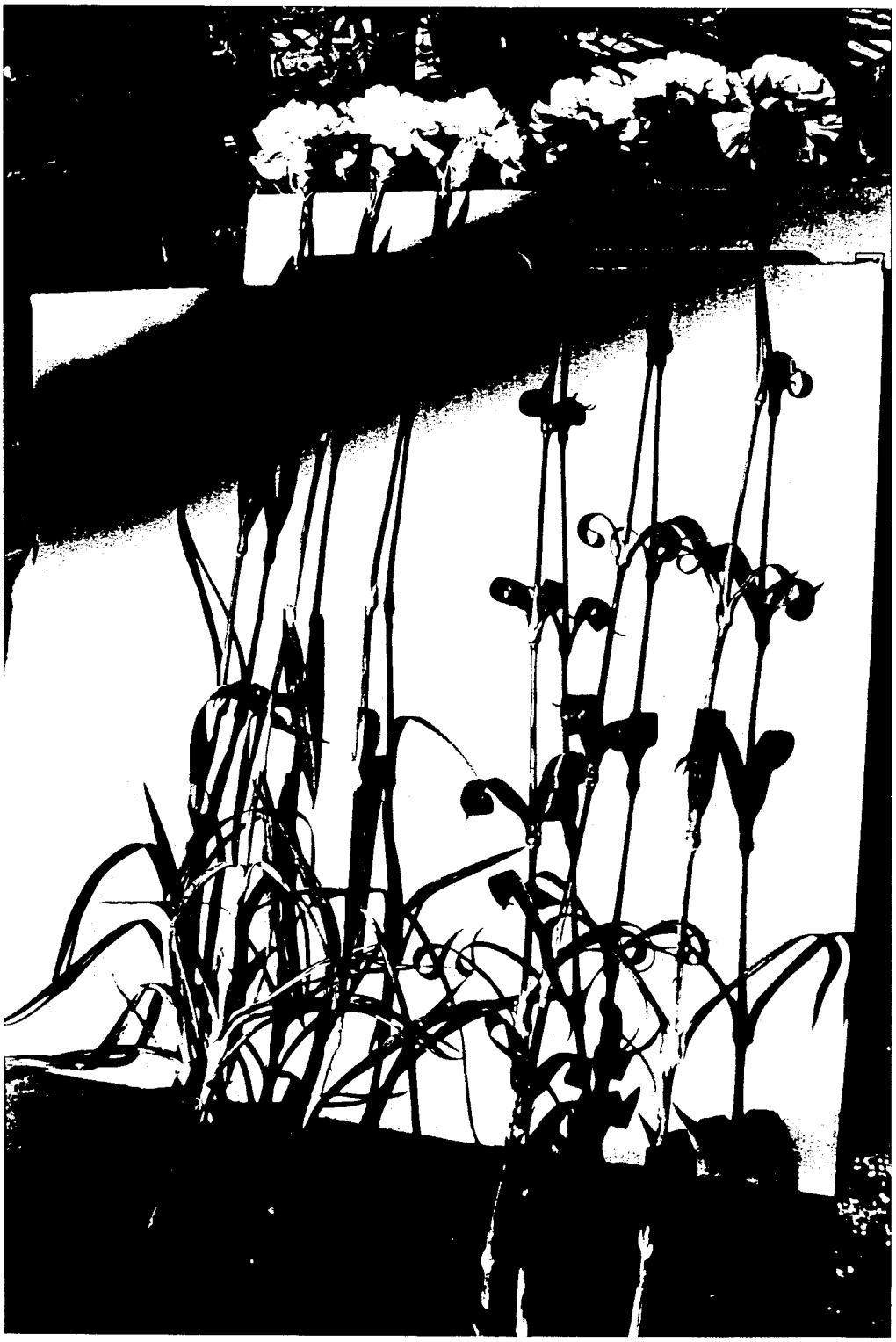
FIGURE 3 (Prior Art)
FIG. 3 is a view of three full length flowers of the prior art Soana Baranna.
FIG. 4 is a view of three full length flowers of the new cultivar. The photograph illustrates the overall characteristics and form of the two cultivars, and shows the longer length stems and curly leaves of the new cultivar, Jun Sakura.
Figures 5, 6:
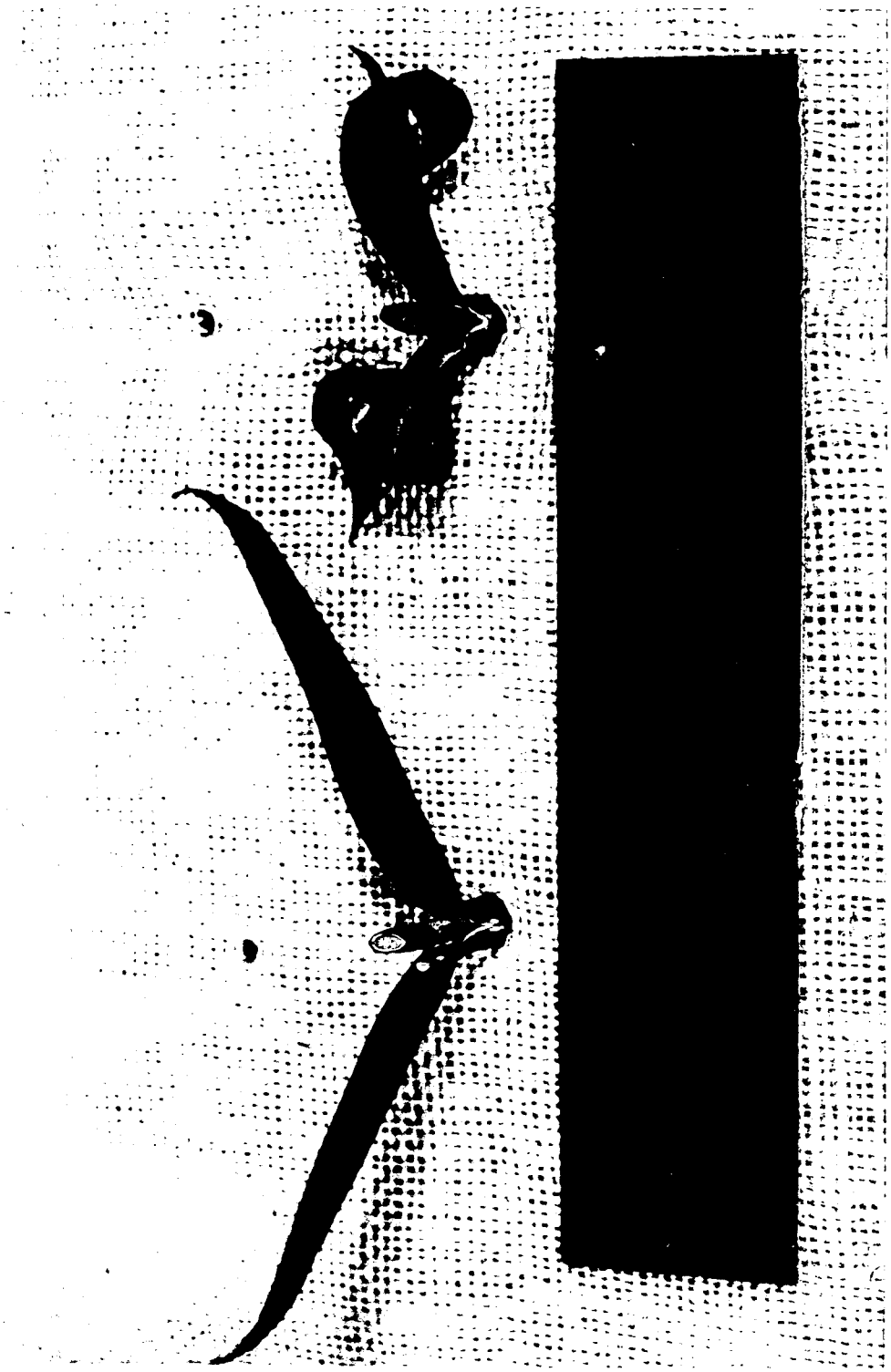
FIGURE 5 (Prior Art)
FIG. 5 is a close up view of the straight leaves of the prior art cultivar, Soana Baranna.
FIG. 6 is a close up view of the leaves of the new cultivar, Jun Sakura, and illustrates the darker green color and curly leaves of the new cultivar compared to the straight leaves of Soana Baranna.

The following is a detailed description of the new carnation plant of the present invention based on observations of plants grown inside commercial greenhouses at Fremont, Calif.; the height of plant, and flower and foliage size established as an average using standard commercial cultural practices. The data provided accurately characterizes the sport in question. The color terminology used in the following is in accordance with The Royal Horticultural Society Colour Chart. Color designation and other values stated may deviate slightly from the stated values from flowering to flowering, but the deviations will be within the range expected from varying environmental, seasonal and cultural conditions.

PLANT

Origin: Sport of Scania, a non-patented, commercial, red-colored carnation of the Sim family.

Classification:

*Botanical.*—*Dianthus caryophyllus.*

*Commercial.*—Carnation, standard disbud type.

Form: Bush; typical carnation, vigorous and upright.

The following table compares the new cultivar with its closest commercial variety of which I am aware.

TABLE OF COMPARISON

| | JUN (New Cultivar) | SOANA BARANNA (Prior Art) |
|---|---|---|
| PLANT: | | |
| Height | 70.5 cm | 60.0 cm |
| FOLIAGE: | | |
| Color | | |
| Upper side | 139 A&B to 139 B | 139B to 139 B&C |
| Lower side | 139 B | 139 A |
| Size | 12.7 cm long × 1.27 cm wide | 10.16 cm long × 1.19 cm wide |
| Quantity | Abundant on mature plants | Same |
| Shape | lanceolate curled | lanceolate straight |
| Texture | Smooth | Same |
| Ribs | single and axial | Same |
| Petioles | amplexicaul (none) | Same |
| Bud | Ovoid, medium sized light green color, typical carnation, smooth | Same |
| BLOOM: | | |
| Form: | Round | Same |
| Size | diameter 10.45 cm average | 9.7 cm |
| | depth average 5.7 cm | 5.0 cm |
| Borne | single after disbudding | Same |
| Shape | high crowned, rounded appearance | slightly less high crowned |
| Color: light pink: | | |
| Upper side: | Red group 56 A to 56 B | 56 C to 56 D |
| Lower Side: | Red group 55 D to 56 A | 56 B to 56 C |
| Blooming habit: | continuous, year around on mature plants, blooms 7–10 days earlier than Soana Baranna | |
| Keeping habit: | 2–3 weeks on plant, 10 days to 2 weeks as cut flowers | Same |
| Persistence | Remains attached and dry | Same |
| Fragrance | slight | Same |
| PETALAGE: | | |
| Appearance and Form | satiny, fan shaped, slightly serrated at apex (much less than most SIM cultivars) | Same |
| Number of Petals: | average 70 | Same |
| REPRODUCTION ORGANS: | | |
| Anthers | 10 each, 2–3 mm long | Same |
| Filaments | 2.0 to 2.5 cm long white in color | Same |
| Pollen | yellowish | Same |
| Pistils | 2–3 each, 3.5 to 4.0 cm long, stigmas pinkish white | Same |
| Ovaries | cone shaped | Same |
| FRUIT: | | |
| Fertility | poor | Same |
| Shape | oblong | Same |
| Color | greenish immature to tannish when mature | Same |

I claim:

1. A new and distinctive cultivar of carnation plant, named Jun Sakura, substantially as herein shown and described characterized particularly as to novelty by it distinctive and attractive pink flower color which retains its color without fading; slightly serrated flowers which open fully without bursting the calyx and causing splits; vigorous strong, straight stems; and good light and heat tolerance.

* * * * *